(12) United States Patent
Collazo

(10) Patent No.: US 7,572,261 B2
(45) Date of Patent: Aug. 11, 2009

(54) MODULAR CAPTURE WITH MAGNETIC ATTACHMENT

(75) Inventor: Carlos E. Collazo, Old Greenwich, CT (US)

(73) Assignee: Howmedica Osteonics Corp., Mahwah, NJ (US)

( * ) Notice: Subject to any disclaimer, the term of this patent is extended or adjusted under 35 U.S.C. 154(b) by 0 days.

(21) Appl. No.: 10/931,185

(22) Filed: Aug. 31, 2004

(65) Prior Publication Data

US 2006/0058806 A1    Mar. 16, 2006

(51) Int. Cl.
*A61F 5/00*    (2006.01)
(52) U.S. Cl. ...................................... 606/87
(58) Field of Classification Search .................. 606/79, 606/86–89, 86 R; 24/303, 327–328, 333; 411/349, 549, 550, 553
See application file for complete search history.

(56) References Cited

U.S. PATENT DOCUMENTS

| 2,644,212 | A | * | 7/1953 | Markowitz | 24/11 R |
|---|---|---|---|---|---|
| 2,975,497 | A | * | 3/1961 | Budreck | 24/303 |
| 3,129,477 | A | * | 4/1964 | Mizuno | 24/303 |
| 4,231,137 | A | * | 11/1980 | Fujimoto | 24/303 |
| 4,378,212 | A | * | 3/1983 | Waldron | 433/128 |
| 4,656,995 | A | * | 4/1987 | Merwin | 606/180 |
| 5,050,276 | A | * | 9/1991 | Pemberton | 24/303 |
| 5,342,368 | A | * | 8/1994 | Petersen | 606/88 |

(Continued)

FOREIGN PATENT DOCUMENTS

EP    538153 A1 *  4/1993

OTHER PUBLICATIONS

Ewald, F., Walker, P., Sledge, C., Kinemax Plus Condylar Knee Kinemax Plus Stabilizer Knee Surgical Technique with the Howmedica Kinemax Plus Knee Instruments Howmedica Surgical Techniques, 1992, pp. 1-19.

(Continued)

*Primary Examiner*—Eduardo C Robert
*Assistant Examiner*—James L Swiger
(74) *Attorney, Agent, or Firm*—Lerner, David, Littenberg, Krumholz & Mentlik, LLP

(57) ABSTRACT

A detachable cutting tool capture for a cutting block provides a guide surface to convert an open surface block into a slotted block for plying a surgical cutting tool along the surfaces of the guide during a surgical procedure such as a bone resection with a blade. A magnetized catch provides a convenient device for securing the capture and the block together. A triangular cam on the detachable capture in conjunction with a "v" groove in a magnetized lever of the catch permits a pin of the catch to be selectively retracted from or extended into an aperture of the block when the lever is rotated so that when the pin extends, it serves to secure the combined apparatus for cutting. Mating surfaces of the block and capture provide additional structure for supporting the capture with the block to secure them from relative movement.

39 Claims, 9 Drawing Sheets

U.S. PATENT DOCUMENTS

| | | | | |
|---|---|---|---|---|
| 5,423,827 A | * | 6/1995 | Mumme et al. | 606/96 |
| 5,681,316 A | * | 10/1997 | DeOrio et al. | 606/88 |
| 5,683,397 A | * | 11/1997 | Vendrely et al. | 606/88 |
| 5,683,398 A | * | 11/1997 | Carls et al. | 606/89 |
| 5,704,941 A | * | 1/1998 | Jacober et al. | 606/88 |
| 5,735,856 A | * | 4/1998 | McCue et al. | 606/87 |
| 5,910,143 A | * | 6/1999 | Cripe et al. | 606/87 |
| 6,258,095 B1 | * | 7/2001 | Lombardo et al. | 606/88 |
| 6,591,462 B2 | * | 7/2003 | Fuhrman | 24/303 |

OTHER PUBLICATIONS

Engh, Moreland, Rorabeck, Volz; Legend II Surgical Technique Concept of Personalization, 1992, pp. 1-30.

Scott, Thronhill, Ranawat: 'Surgical Technique For Use With P.F. C.® Sigma Knee Systems' Primary Cruciate-Retaining & Cruciate-Substituting Procedure, 1998, pp. 1-99.

* cited by examiner

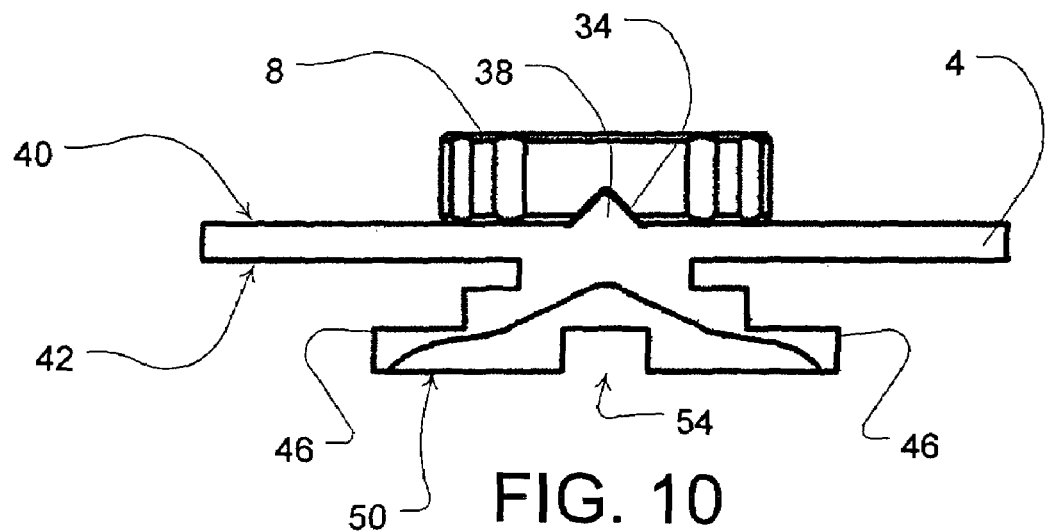
FIG. 10
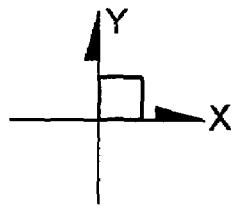
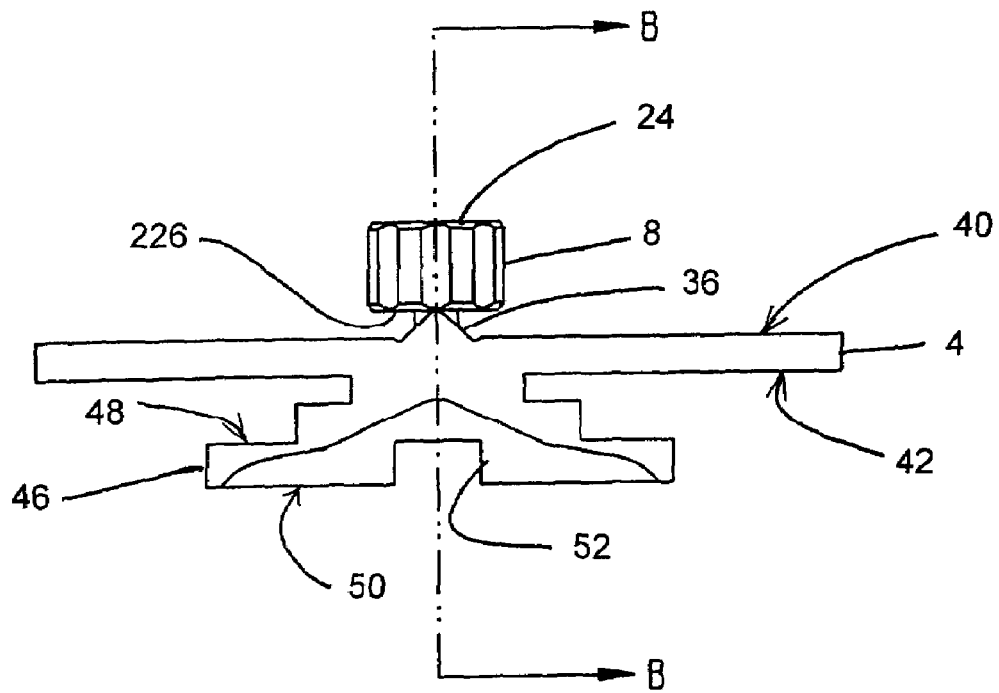
FIG. 11

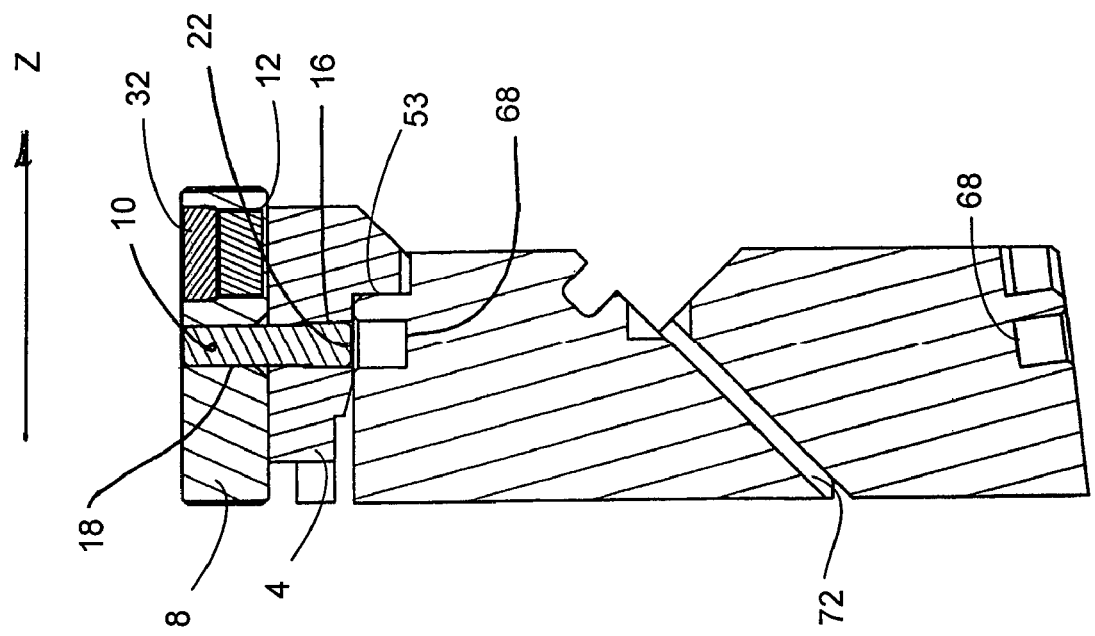
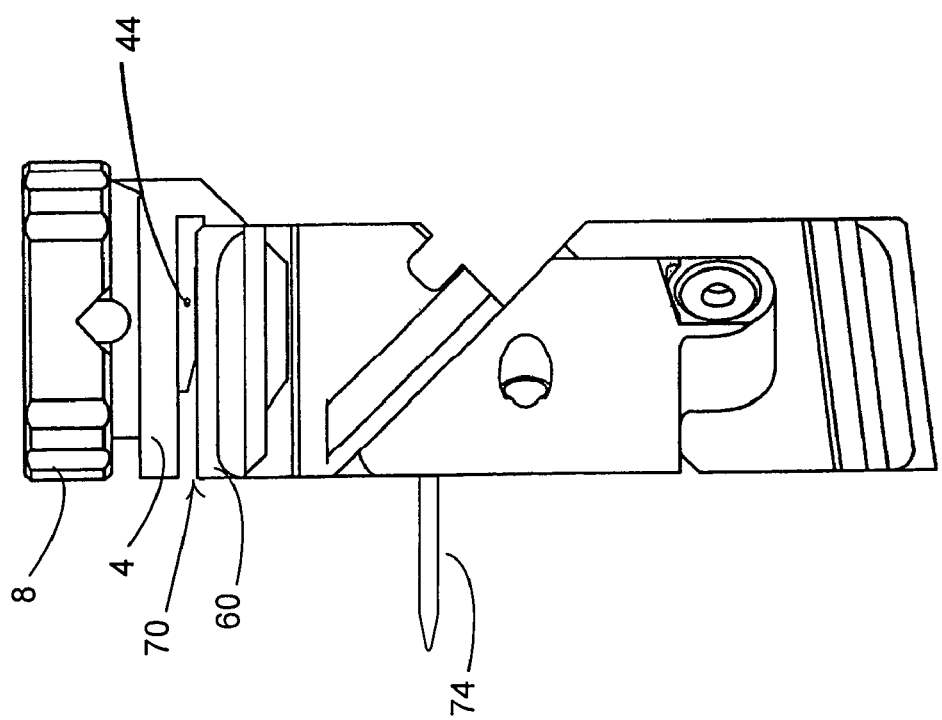

MODULAR CAPTURE WITH MAGNETIC ATTACHMENT

FIELD OF THE INVENTION

The present invention relates to surgical devices. More particularly, the invention involves a cutting block or guide with a detachable cutting instrument capture for precision cutting during a surgical procedure.

BACKGROUND OF THE INVENTION

Precision cutting instruments that promote accuracy are necessities in surgical procedures. For example, consider total knee arthroplasty. Total knee arthroplasty involves the replacement of portions of the patella, femur and tibia with artificial components. During the procedure, a proximal portion of the tibia and a distal portion of the femur are cut away (resected) and replaced with artificial components. The posterior surface of the patella may also be resected and resurfaced. As used herein, when referring to bones or other body parts, the term "proximal" means closest to the heart and the term "distal" means more distant from the heart. When referring to tools and instruments, the term "proximal" means closest to the practitioner and the term "distal" means distant from the practitioner.

There are several types of knee prostheses known in the art. One type is sometimes referred to as a "resurfacing type". In these prostheses, the articular surface of the distal femur and proximal tibia are "resurfaced" with respective metal and plastic condylar-type articular bearing components. During primary knee replacement, these knee prostheses require minimal and precise bone resection to accommodate the components within the boundaries of the available joint space.

Often, due to normal wear over time, the prosthetic knee must be replaced via a procedure known as revision surgery. One method for accomplishing revision arthroplasty involves the use of several cutting blocks which may be aligned with reference to the IM canal.

During revision surgery, after the primary prosthetic is removed, the medullary canal is reamed and an intramedulary rod or the reamer itself is tapped in place with a mallet. A distal resection guide is attached to the reamer or the intramedulary rod and distal resection is completed via slots in the guide. The distal resection guide is removed from the rod or reamer and another cutting block is attached for the typical anterior-posterior resection and the anterior and posterior and chamfer resections.

The rotational alignment of the femoral component is critical to ensure correct patellar tracking. Since the posterior condyles are no longer present, this cutting block must be carefully aligned relative to the femoral epicondyles where the collateral ligaments are attached.

After anterior/posterior and chamfer resections are completed, if the posterior cruciate ligament is being sacrificed, the cutting block is removed and a fourth cutting block is attached to the reamer or rod in order to accomplish an intercondylar box resection. Of course, the box resection guide can be incorporated into the same guide used to make the A/P and chamfer cuts.

Following preparation of the femur, similar procedures are performed on the proximal tibia. For example, a reamer or intramedulary rod is installed with a mallet. Preferably, a resection block is pinned to the anterior tibia and a proximal portion of the tibia is resected.

It will be appreciated that given the use of multiple cutting blocks in the described procedure the design of each device should not also add to the complexity of the operation. Generally, such cutting blocks used in surgical procedures may be characterized as open or slotted. In an open block, one surface serves as an open face guide to rest or ply a cutting instrument. In contrast, a slotted block provides an envelope, or "slot" having multiple surfaces within which the block captures the cutting tool or blade to help maintain the blade tracking straight or in desired configuration or arrangement during cutting through the envelope or slot.

In theory, open face blocks induce a greater margin of error than slotted blocks since it is more dependent on surgeon skill to maintain the cutting tool aligned with the guiding surface (e.g., keeping the blade flat against the block). Moreover, a substantially open cutting block may be easier to clean or sterilize when compared to a slotted block. Nevertheless, whether an open face or slotted cutting block is used during surgery is a matter of surgeon preference. To accommodate physician preference it may be appropriate for a medical institution or hospital to have both types of blocks available for the many different procedures for which blocks are designed. However, a drawback of having both slotted and open-face blocks is that it doubles the inventory required to meet the institution's needs. This means more sterilization procedures, more storage issues and ultimately higher costs.

SUMMARY OF THE INVENTION

This apparatus conveniently joins an open-face cutting block and a capture, thus giving the user the option to use either open face guide or a slotted guide during a surgical procedure. In one embodiment, the apparatus includes a cutting block which has a guiding surface to guide a surgical cutting instrument. The apparatus further includes a detachable capture which also includes a guiding surface to guide a surgical cutting instrument. The capture is configured for removable coupling with the cutting block. Preferably, the capture includes a biased catch having a biasing force such as a magnetized catch for magnetically securing the cutting block and capture together or a catch with a spring configured for securing them with an elastic force. In one embodiment, the capture includes a projection for gradually changing the catch from a secured to an unsecured position. The assembled apparatus may be used as a slotted guide during a surgical procedure such as a bone resection.

In one embodiment of the invention, an apparatus for guiding an oscillating saw blade for resecting bone includes an open face means for supporting a saw blade during a resection procedure of a bone. The open face means may be temporarily fixed to a bone for the procedure. A detachable capture means converts the open face means to a slotted guide. The apparatus also includes a securing means for removably fixing the capture and the open face means into a coupled position. This preferably includes a rib and a slotted tab corresponding with the rib such that when the rib is inserted in the slotted tab in the coupled position, movement of the detachable capture means is prevented with respect to the open face means in any direction along a first axis. The securing means further includes a plate and mating surfaces corresponding with the plate such that when the plate is inserted between the mating surfaces in the coupled position, movement of the detachable capture means is impeded with respect to the open face means in any direction along a second axis being perpendicular to the first axis. Finally, the securing means includes a pin aperture and a traversing pin corresponding with the pin aperture so that when the pin is inserted in the pin aperture in the coupled position, movement of the detachable capture means is impeded with respect to the open face means.

In still another embodiment, an apparatus for guiding a cutting tool during a surgical procedure includes a cutting block having a surface for guiding a cutting tool. The cutting block is configured to be fixable to bone for making a cut in the bone. The detachable capture has another surface to guide the cutting tool. The detachable capture is configured for coupling with the cutting block in a coupled position in which the surfaces combine to form an envelope for the cutting tool. The apparatus also includes a cam with a configuration to selectively secure and unsecure the cutting block and the detachable capture in the coupled position. A catch corresponds with the cam for securing the detachable capture and the block in the coupled position. In this regard, the catch includes a reciprocal portion corresponding to a projection of the cam such that when the reciprocal portion and projection coincide, the catch secures the cutting block and the detachable capture in the coupled position. Moreover, the catch includes a non-reciprocal portion corresponding to the projection of the cam such that when the non-reciprocal portion and projection coincide, the detachable capture and the cutting block are not secured. In a preferred embodiment, the reciprocal portion of the catch has a triangular shape.

In yet another embodiment, the cutting guide apparatus for a surgical procedure has a cutting block with a first open face surface for guiding a surgical instrument. A detachable capture includes a second open face surface for guiding an instrument for a surgical procedure. The detachable capture is configured to couple with the cutting block to form a slotted guide from the first open face surface of the cutting block and the second open face surface of the detachable capture.

Additional aspects of the invention will be apparent from an understanding of the details contained in the detailed description.

BRIEF DESCRIPTION OF THE DRAWINGS

For the purposes of illustrating the invention, there are shown in the drawings, a form that is presently preferred, it being understood, however, that the invention is not limited to the precise arrangements and instrumentalities shown.

FIG. 10 is a front elevation view of an embodiment of a modular capture with the catch lowered in a secured position;

FIG. 11 is a front elevation view of an embodiment of a modular capture with the catch raised on the cam in its unsecured position;

FIG. 13 is a side elevation view of the modular capture coupled to a cutting block of FIG. 12 in an unlocked position;

FIG. 14 is a section view of the modular capture coupled to a cutting block of FIG. 12 taken along line C--C;

DETAILED DESCRIPTION

Figure 1:
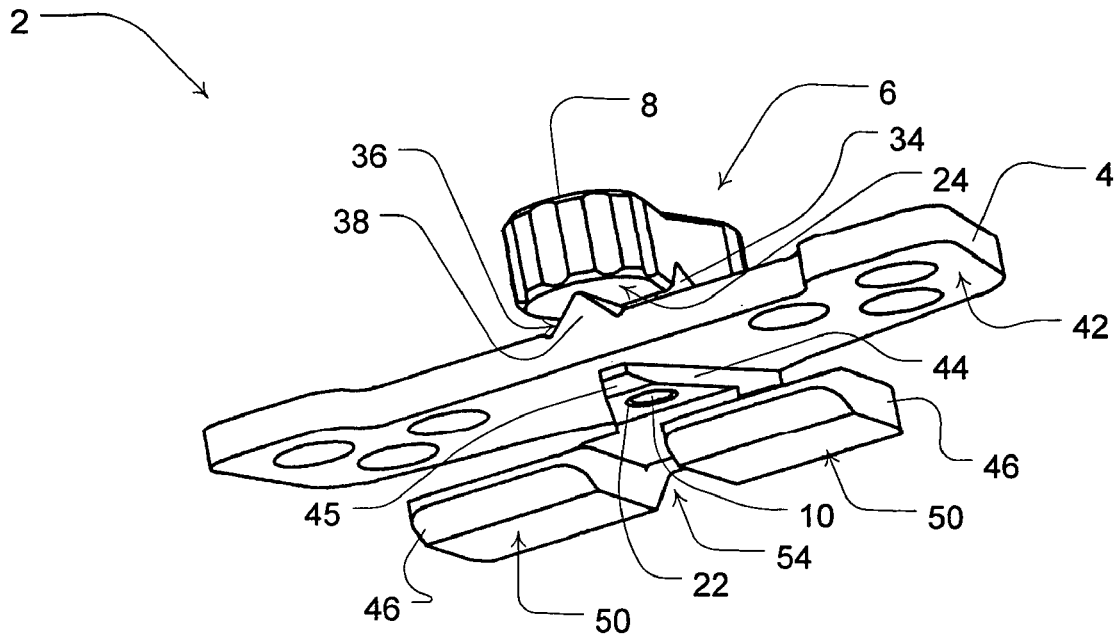
FIG. 1 is perspective view of an embodiment of a modular capture of the invention.
Figure 2:
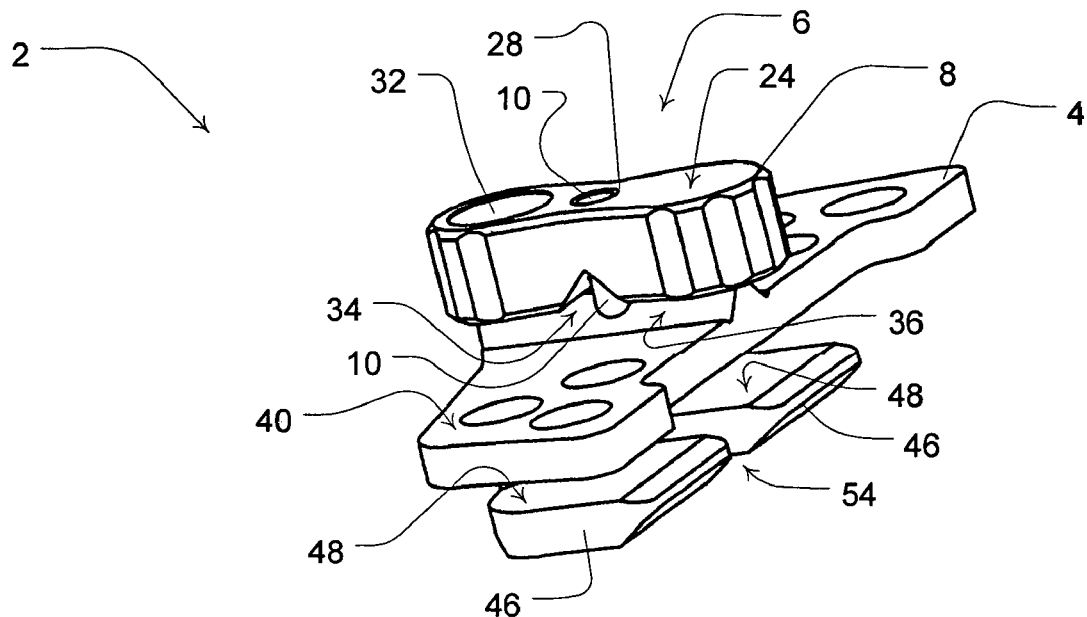
FIG. 2 is another perspective view of an embodiment of a modular capture of the invention.
Figure 3:
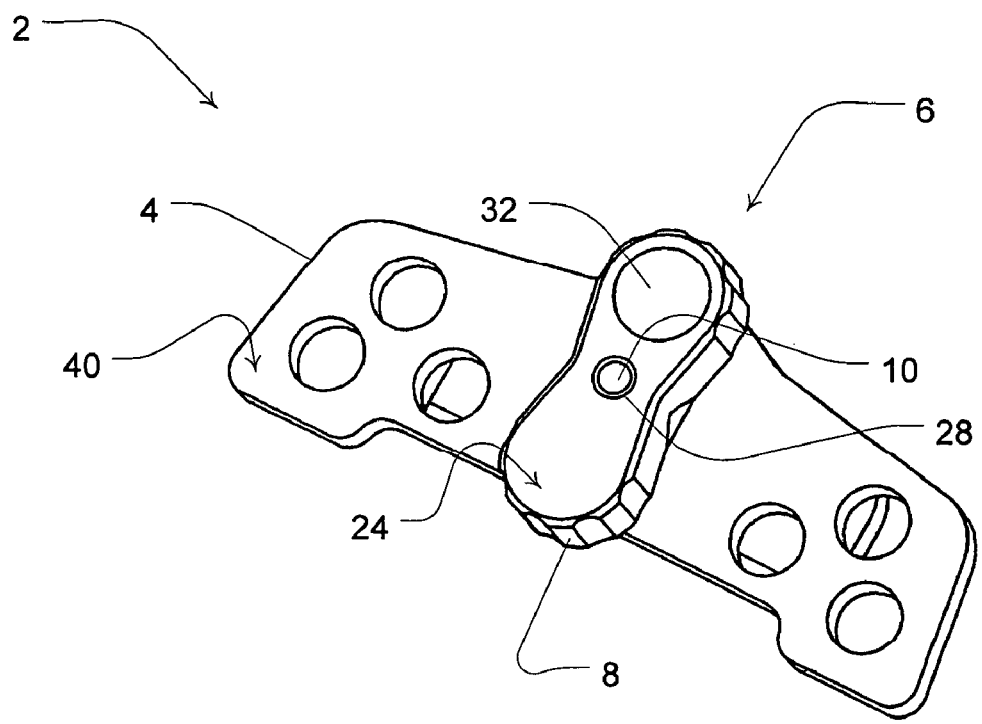
FIG. 3 is a further perspective view of an embodiment of a modular capture of the invention.
Figure 4:
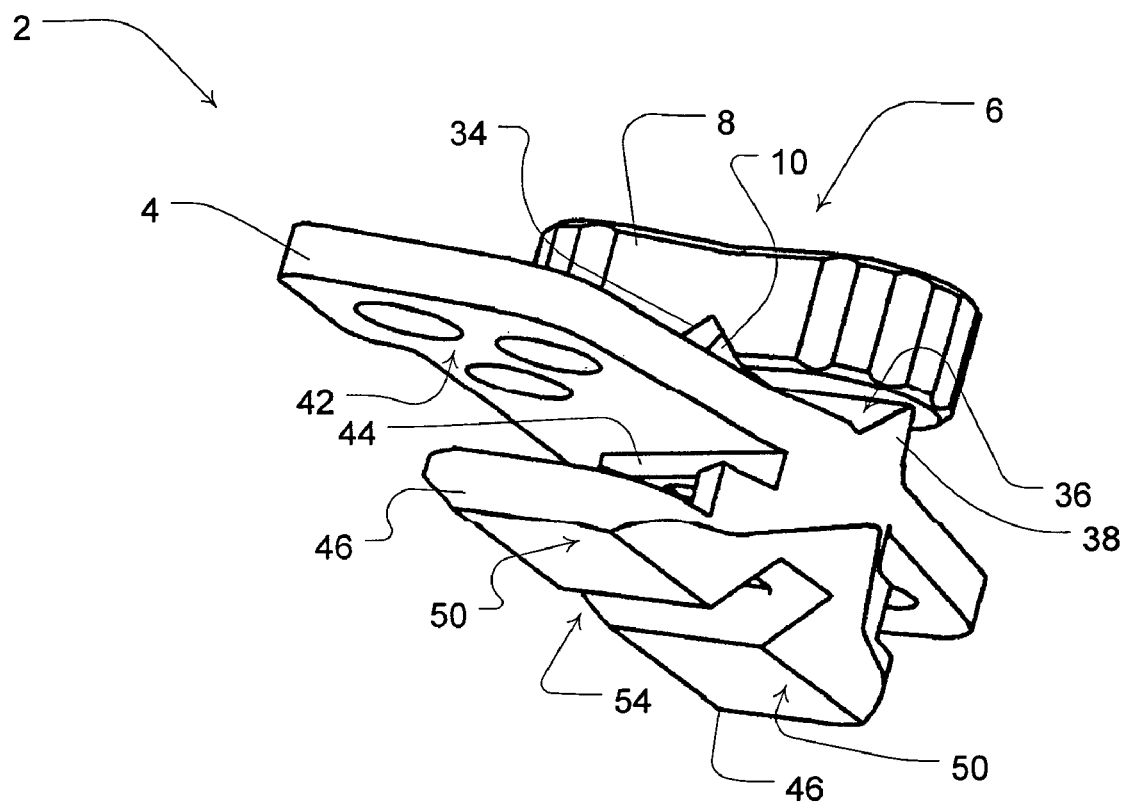
FIG. 4 is an additional perspective view of an embodiment of a modular capture of the invention.
Figure 5:
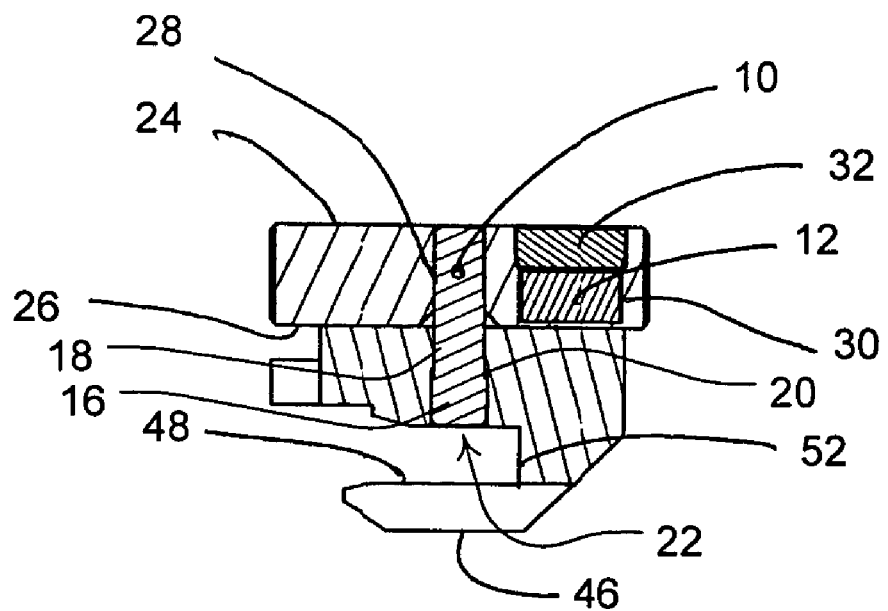
FIG. 5 is a section of an embodiment of a modular capture of the invention taken along line B--B of FIG. 11 with the catch raised on its cam in an unsecured position.
Figure 6:
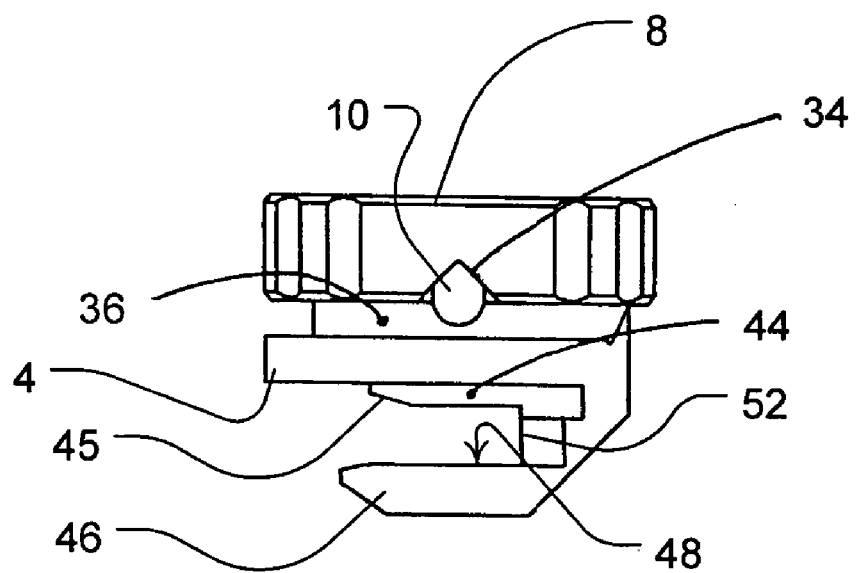
FIG. 6 is a side elevation view of an embodiment of a modular capture with the catch raised on its cam in its unsecured position.
Figure 7:
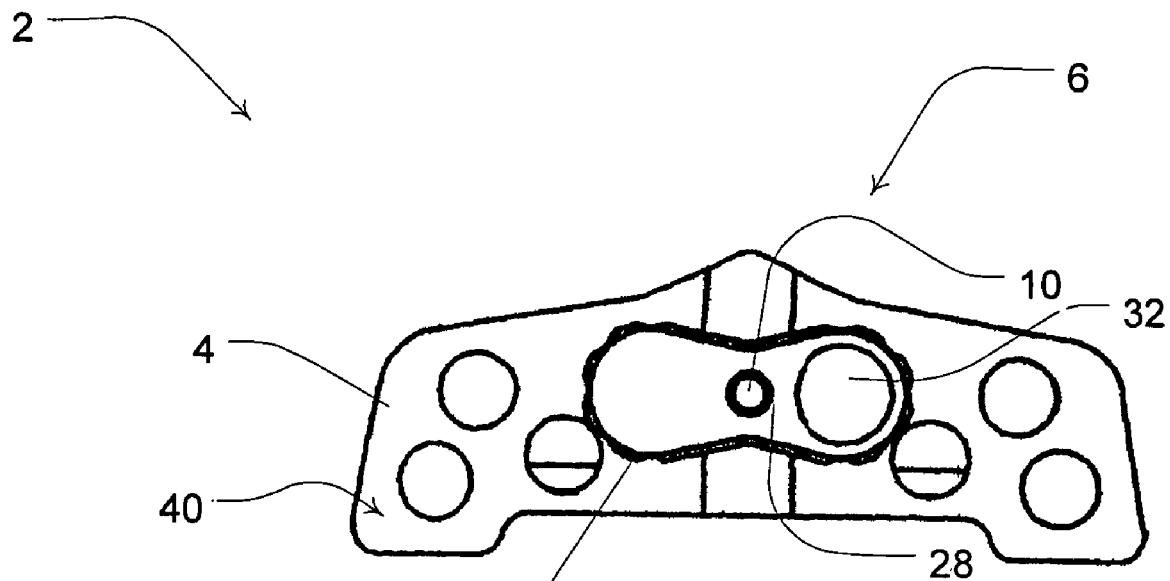
FIG. 7 is a top plan view of an embodiment of a modular capture with the catch lowered in a secured position.
Figure 8:
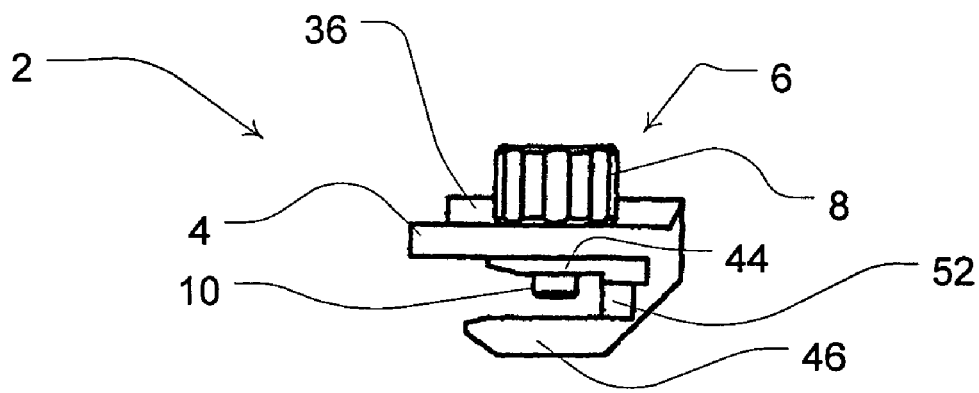
FIG. 8 is a side elevation view of an embodiment of a modular capture with the catch lowered in a secured position.
Figure 9:
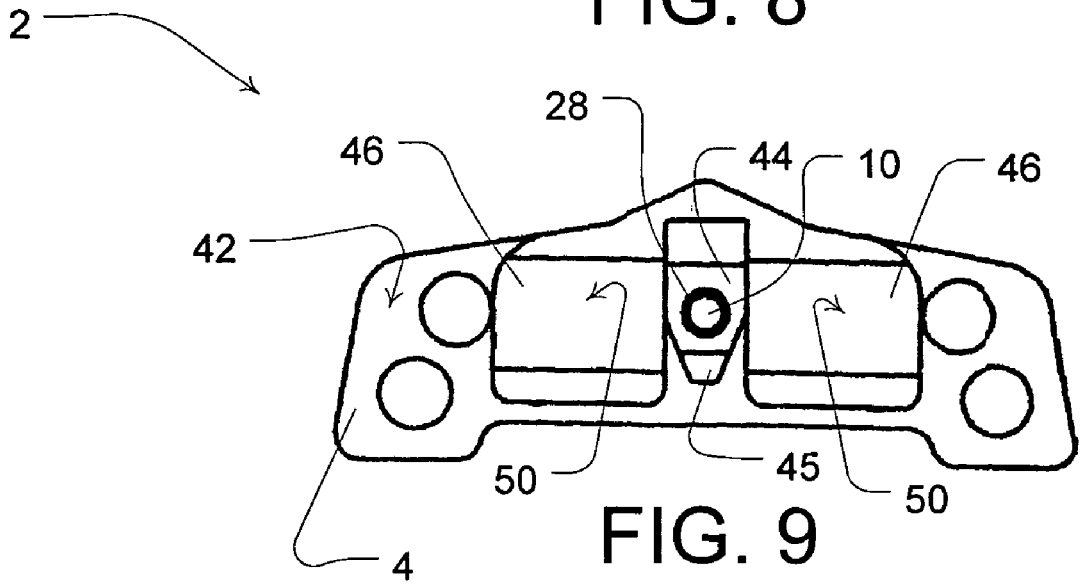
FIG. 9 is a bottom plan view of an embodiment of a modular capture.

The invention generally involves a detachable or modular capture apparatus that attaches to an open-face cutting block and provides a slot for guiding a cutting tool such as an oscillating saw blade to make a bone cut. The device preferably converts the open-face cutting block to a slotted block, thus giving a user the option to use either.

With particular reference to FIGS. 1 through 11, in a preferred embodiment of the detachable capture 2, the device consists of a main housing 4 and a locking mechanism or catch 6. The preferred embodiment of the catch 6 includes a locking lever 8, locking pin 10, and integrated magnet 12 that can bias the catch 6 in a locked or unlocked position.

To prevent the catch 6 from disassembling from the main housing 4, the locking pin 10 of the catch 6 preferably consists of two coaxial cylindrical portions. The first cylindrical portion 16 has a larger diameter than the second cylindrical portion 18 to form a shoulder 20. The main housing 4 also includes a corresponding counter-bored hole 22. The counter-bored hole 22 and the locking pin 10 are closely dimensioned to allow translation of the pin 10 along the axis of the counter-bored hole 22. The close dimensioning also permits rotation of the pin 10 in the counter-bored hole 22. However, the pin shoulder 20 prohibits disassembly in one direction as a result of the corresponding diameters of the counter-bored hole 22.

The lever 8 also impedes removal of the pin 10 from the main housing 4 of the detachable capture 2 when the lever 8, which is larger than the counter-bored hole 22, is fixed to the pin 10. For convenience, the pin 10 is press fit with the lever 8. In this regard, the lever 8 has an upper lever surface 24 and a lower lever surface 26, which may be parallel to each other. A locking pin hole 28, preferably perpendicular to the upper surface 24, optionally extends from the upper surface to the lower surface 26. The locking pin hole 28 is dimensioned to accept the second cylindrical portion 18 of locking pin 10 by press fitting.

As a result, depending on the length of the pin 10, the locking lever 8 may be employed as a handle to extend or retract the locking pin 10 through the counter-bored hole 22 of the main housing 4, but due to the impediments of the lever 8 and the pin shoulder 20, the catch 6 remains movable or traversable but also a component of the main housing 4. Thus, the length of the locking pin 10 is chosen such that when it is housed in the counter-bored hole 22 and placed perpendicularly through a lower surface of main housing 4, it extends through the entire thickness of main housing 4 and into the lever 8.

With regard to the magnetization of the catch 6, for preference a magnet 12 is housed in a magnet aperture 30. The magnet aperture 30 may be machined adjacent and parallel to locking pin hole 28 of locking lever 8. The magnet aperture 30 is counter-bored, extending from upper surface 24 of locking lever 8 to a depth that is less than the overall thickness of locking lever 8 leaving a thin wall to allow the magnet to be in close proximity to the main housing 4. A cylindrical cap 32 is pressed fitted into the counter-bore magnet aperture 30 to preferably hermetically seal the magnet. Thus, the locking lever 8 may be made of non-magnetic material, such as titanium, or type 304 stainless steel.

Beneficially, a recessed or inwardly projecting "v" Groove 34 is machined on lower surface 26 of locking lever 8. This inward projection is reciprocally configured and dimensioned to couple with a matching cam 36 on a surface of main housing 4 of the detachable capture 2 giving them a profile with the same shape. In the preferred embodiment, the cam 36 includes an outwardly projecting triangular section 38. The locking lever 8, also includes a non-reciprocal portion not matching the cam 36. The locking lever 8, when positioned over the cam 36 so that the "v" groove 34 and triangular section 38 of the cam 36 match, will magnetically attach with the lower lever surface 26 of the locking lever 8 to upper main surface 40 of the main housing 4, extending the pin 10 outward from an opposing surface of the main housing. In this position, the triangular section 38 is received in the "v" groove of the lever. This secured position of the catch 6 is best viewed in the illustrations in FIGS. 7, 8 and 10. When a non-reciprocal portion of the locking lever 8 is rotated to a position over the projection of the cam 36, the lower lever surface 26 gradually departs from upper main surface 40 of the main housing 4, rising on the cam 36, and thereby retracts the locking pin 10 into the main housing 4 at the opposing surface of the main housing 4. This unsecured position of the catch 6 is best illustrated in FIGS. 1 through 6 and 11 through 14.

The main housing 4 includes an upper main surface 40 and a lower main surface 42, which, is adjacent and parallel to upper main surface 40. The lower main surface 42 may serve as part of a slotted guide or guide envelope for a cutting tool when coupled to a cutting block mated for the detachable capture 2. The upper main surface 40 is formed of a magnetic material such that it will be attracted by the magnet 12 of the magnetized catch 6.

Extending from the central region of lower main surface 42 is a raised pad 44 of constant thickness forming a step with lower main surface 42. The raised pad 44 is chosen to be a preferred slot thickness for the cutting envelope formed when the detachable capture is coupled to the cutting block because the raised pad 44 will serve to separate the opposing surfaces of the formed cutting envelope. Optionally, the raised pad 44 may include a beveled end 45 to facilitate coupling of the capture 2 with a cutting block as the cutting block is positioned onto the cutting block.

Adjacent to lower main surface 42 is a tab 46 with a rectangular configuration. Tab 46 contains an upper tab surface 48 and a lower tab surface 50 to form a thickness and is connected to the main housing by a bridged portion 52. Upper tab surface 48 and lower tab surface 50 of tab 46 are parallel with lower main surface 42 of main housing 4. Tab 46 is bisected by a tab slot 54, which extends from upper tab surface 48 to lower tab surface 50 of tab 46.

As will be described in more detail herein, together the surfaces of the tab 46, the surface of the raised pad 44, and the catch 6 in conjunction with mating or corresponding features of a cutting block 56, serve as a means for securing the detachable capture 2 with a cutting block to form a cutting envelope.

In this regard, the mating features of a preferred cutting block 56 that can be magnetically secured in a coupled position with the detachable capture 2 are illustrated in FIGS. 12-15. The cutting block 56, which includes an open face guide 58 against which a cutting tool may ply, consists of a plate 60 having an upper plate surface 62 and a lower plate surface 64 which is adjacent and parallel with upper plate surface 62 and a central rib 66, which is preferably perpendicular to upper plate surface 62. As illustrated in the preferred embodiment, the upper plate surface 62 may serve as an open face guide 58. The cutting block 56 also includes a pin aperture 68 sized and positioned to receive the locking pin 10 of the catch 6. The surfaces of the plate 60, the rib 66, and pin aperture 68 serve as the mating features of the block for securing the capture and the block.

Figure 16:
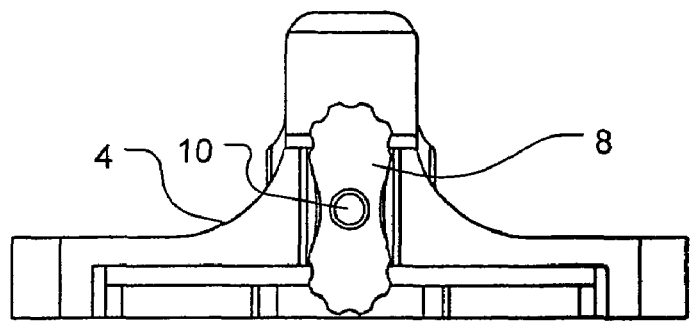
FIG. 16 is a top elevation view showing an alternative embodiment of the capture having a spring-biased locking mechanism.
Figure 17:
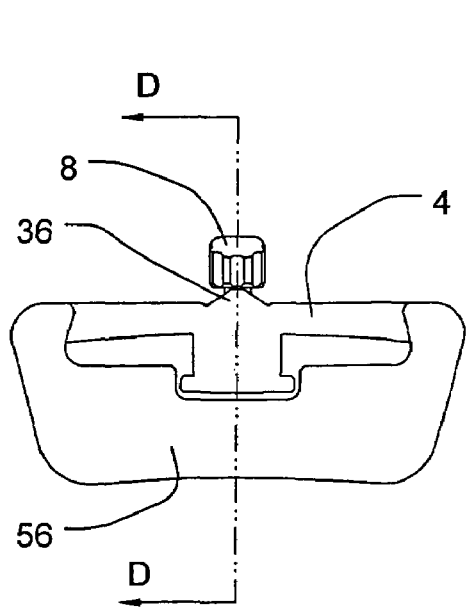
FIG. 17 is a front elevation illustration of the capture of FIG. 16.
Figure 18:
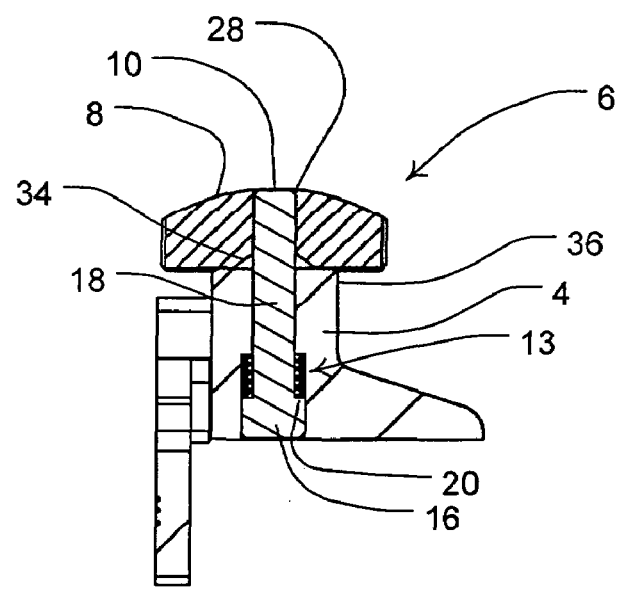
FIG. 18 is a sectional view of the capture of FIG. 16 taken along line D--D of FIG. 17.

In an alternative embodiment of the capture, the catch 6 (with or without the magnet 12) may include a locking spring 13 to bias or further bias the pin 10. In such an embodiment, the spring may be configured with the pin 10 or lever 8 to bias the catch 6 with an elastic force to remain in the locked position when the detachable capture 2 and cutting block 56 are coupled. An example of the embodiment with a spring is illustrated in FIGS. 16 to 18. As illustrated in FIG. 18, locking spring 13 is installed around the first cylindrical portion 18 of the locking pin 10. Although other implementations are possible, in this example the locking spring 13 provides an elastic compression force between shoulder 20 of the locking pin 10 and the pin aperture of the main housing 4 to bias the locking pin 10 to extend from the main housing 4 into the pin aperture 68 of the cutting block 56. Thus, when the lever 8 of the catch 6 is lifted from the upper main surface 40 of the main housing 4 or rotated to its unlocked position on the peak of the cam 36 as illustrated in FIGS. 17 and 18 an elastic force is compressed into the spring providing a bias for its return to the locked position. As such, it will tend to return to the locked position unless the lever 8 is positioned on the peak of the cam 36, out of the "v" grove 34 of the lever 6.

In operation, the main housing 4 may be engaged with the cutting block 56 such that raised pad 44 and upper tab surface 48 of tab 46 straddle the plate. Thus, the raised pad 44 contacts the upper plate surface 62 and the upper tab surface 48 contacts the lower plate surface 64. Similarly, tab 46 straddles the central rib 66 when the rib 66 resides in the tab slot 54. Finally, the locking lever 8 may be rotated so that the "v" groove 34 of the lever is positioned over the triangular section 38 of the cam 36. In this position, lever 8 may be lowered to magnetically attach to the upper main surface 40 of the main housing when the triangular section 38 enters the "v" groove 34. Consequently, the locking pin 10 traverses to extend out of the main housing through the raised pad 44 to extend into and couple with the pin aperture 68, thereby securing the cutting block 56 and the detachable capture in a coupled position.

Figure 12:
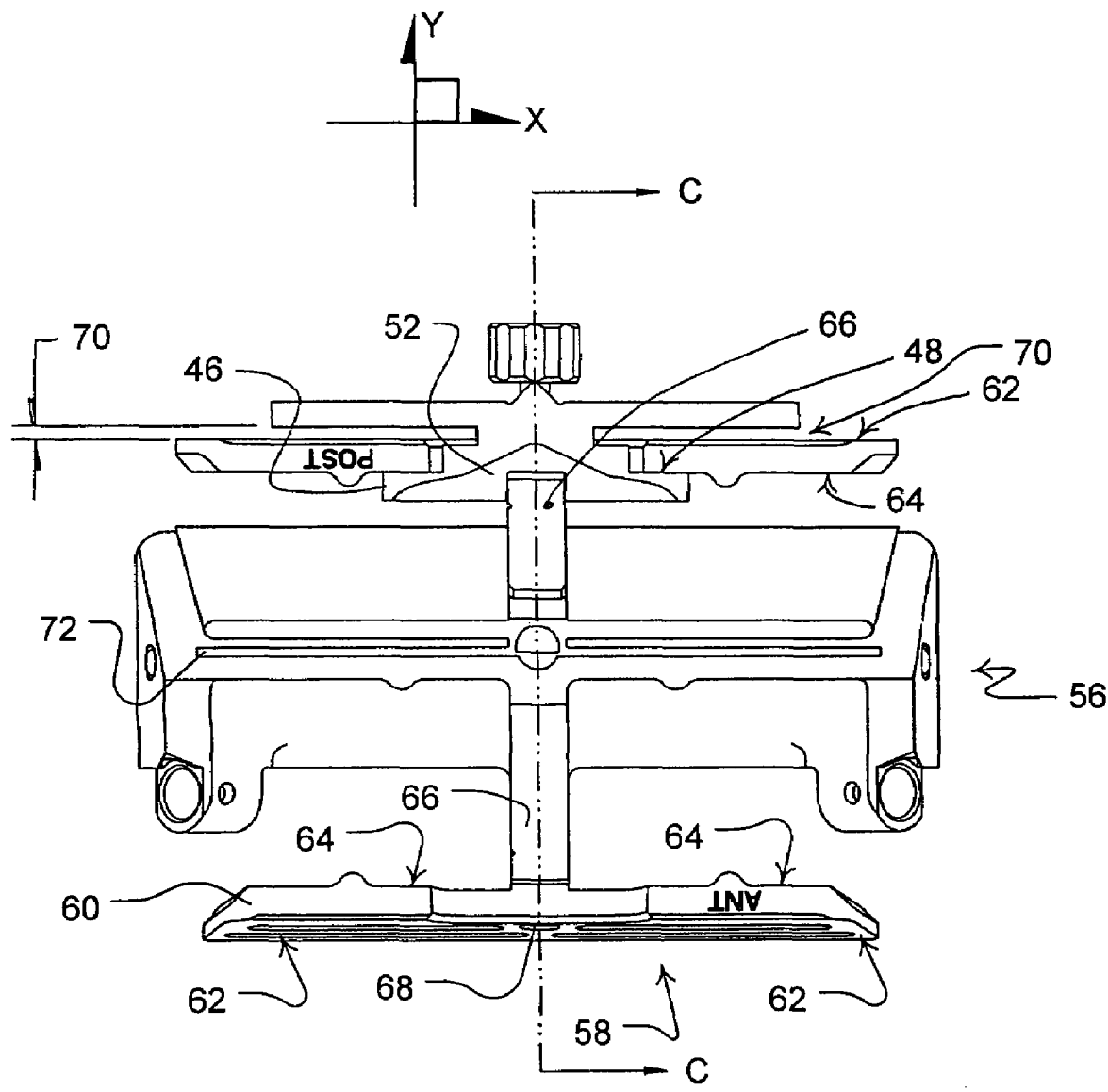
FIG. 12 is a front elevation view of an embodiment of a modular capture coupled to a cutting block with the catch raised on the cam in an unsecured position.
Figure 15:
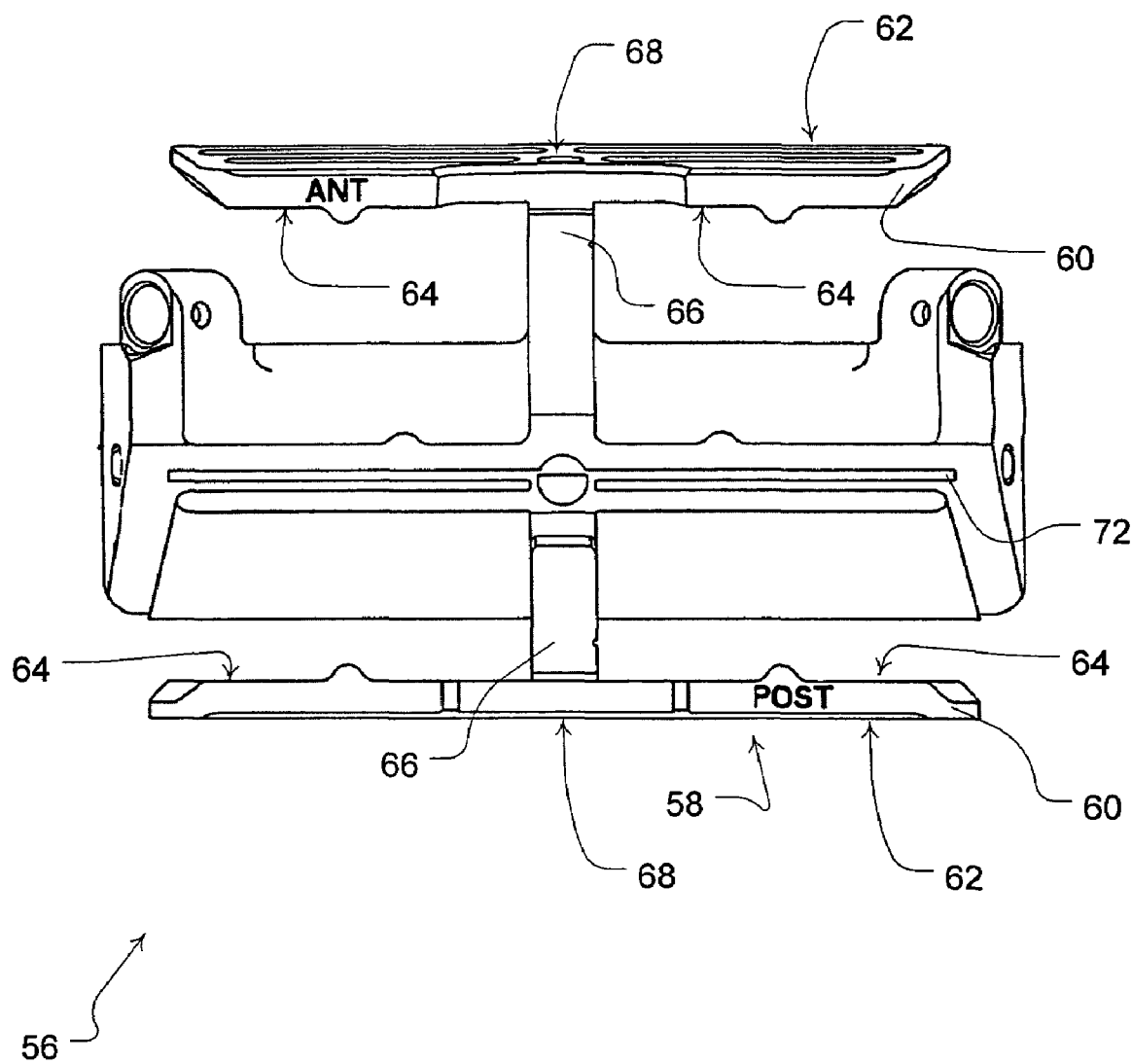
FIG. 15 is a front elevation of an embodiment of a cutting block to which a modular capture may be coupled.

When so assembled, movement of the main housing 4 with respect to the cutting block in the X-Y directions illustrated in FIGS. 11 or 12 is limited only by the clearance that exists between mating surfaces. Thus, when the rib 66 is inserted in the tab slot 54, the opposing surfaces of the tab slot 54 and rib 66 impede movement of the detachable capture 2 with respect to the cutting block 56 in any direction along the imaginary X axis illustrated by the X axis of FIGS. 11 or 12. Similarly, when the upper tab surface 48 of the tab 46 and the surface of the raised pad 44 straddle the plate, the opposing surfaces of the tab 46, raised pad 44 and plate 60, impede movement of the capture 2 with respect to the block 56 in any direction along the imaginary Y axis of FIGS. 11 or 12. The X and Y axes and the directions discussed above with respect to each are generally perpendicular to each other.

Finally, the insertion of the locking pin 10 into the pin aperture 68 prevents or impedes movement of the detachable capture 2 with respect to cutting block 56 in any direction along the imaginary Z axis illustrated in FIG. 14. Optionally, a surface of the bridge portion 52 and a side 53 of the plate (see in FIG. 14) may mate so as to impede relative movement of the cutting block 56 and the detachable capture along a direction of the imaginary Z axis. With such contact between the side 53 of the plate 60 and the bridge portion 52, a stop is provided to simplify alignment of the locking pin 10 with the pin aperture 68 for insertion. Generally, the Z axis and the directions of movement described above with respect to it are perpendicular to the X and Y axes of FIG. 11 or 12.

In this magnetically and/or elastically biased secured or locked position, the lower lever surface 26 of the locking lever 8 is in full contact with the upper main surface 40 of main housing 4. With such contact, the locking lever 8 remains biased to the locked position by the magnetic force of magnet 12 and/or the elastic force of the locking spring 13.

The cutting block 56 and main housing 4 when assembled are dimensioned such that a guide slot 70 is formed for guiding a cutting tool, (e.g., a saw blade) by the upper plate surface 62 and the lower main surface 42. This guide slot 70 is illustrated in FIG. 12. Cutting block 56 may optionally include multiple plates which may be converted by a single detachable capture 2 simply by re-attaching the capture 2 in a different position with respect to different plates to create different envelopes or slotted guides. In the preferred embodiment, the block also includes an integrated guide slot 72. When the capture is not assembled with the block, the upper plate surface 62 may be utilized as an open face cutting guide. Of course, for a resection procedure on bone as previously described, the block would also include a fixing device 74 to temporarily fix the block to the bone for the surgical cutting procedure.

To remove the capture 2, the locking lever 8 is turned 90 degrees. When it rotates about the axis of counter-bored hole 22 in main housing 4, the camming action of the "v" groove and triangular cam results in the entire locking lever 8 being forced away from upper main surface 40, thus retracting the locking pin 10 into the main housing 4 which disengages it from the pin aperture 68 on cutting block 56. Conveniently, the magnet 12 of the lever 8 holds the lever 8 at the peak of the cam 36 in an unlocked or unsecured position by a magnetic force to impede the lever 8 from unintentionally returning to the locked position of the cam 36.

With such a design for a detachable capture, cleaning is made easier. For example, by virtue of the readily removable nature of the capture, complete open access to the guide surfaces of the slotted guide is permitted. Thus, such a design is easier to clean than an integral capture, retractable or otherwise. Moreover, in a cutting block as illustrated in FIGS. 12-15, where the capture may be installed in multiple positions on multiple open face guides of the cutting block, a single capture may be reused, cutting down on the number of parts which need to be cleaned.

The locking features and method of attachment allows the capture to be rapidly and easily secured to the cutting block with minimal risk of disassociation during use. The magnet provides a positive locking implementation. In conjunction with the cam and mating surfaces, the locking feature provides an ergonomic, self-aligning locking mechanism.

Moreover, with the preferred design, the capture can be made very small since the locking mechanism itself is very small and is centralized with respect to the width of the capture. A smaller capture allows the cutting block to also be made smaller. This is a benefit since the current trend is to make minimally invasive incisions thus requiring smaller instruments. Adding to the smaller size theme is the use of a magnet to bias the locking lever in the locked position. This results in a very low profile locking lever, a benefit compared to the use of springs which require more room.

Although the invention herein has been described with reference to a particular preferred embodiment, it is to be understood that this embodiment is merely illustrative of the principles and applications of the present invention. It is therefore to be understood that numerous modifications may be made to the illustrative embodiments and that other arrangements may be devised without departing from the spirit and scope of the present invention as defined by the appended claims. For example, one skilled in the art will recognize that the mating surfaces associated with the rib 66 and tab slot 54 can be optional since the pin 10, when residing in a pin aperture 68 that closely corresponds with the surfaces of the pin 10, can limit relative movement between the capture 2 and the cutting block 56 along two perpendicular axes (e.g., axes Z and X) being generally perpendicular to a remaining axis (e.g., the Y axis). Relative movement with respect to this remaining axis would still be limited by the mating surfaces of the plate 60, the raised pad 44 and the upper tab surface 48 of the tab 46. Other modifications will also be apparent.

Throughout the description and claims of this specification, forms of the word "comprise" including all variations of the word, such as "comprising" and "comprises", are not intended to exclude other additives, components, integers or steps etc.

The invention claimed is:

1. An apparatus for guiding a cutting instrument during a surgical procedure comprising:
    a cutting block with a first guiding surface against which a cutting instrument may engage during a surgical procedure;
    a capture having a second guiding surface against which a cutting instrument may engage during a surgical procedure, the capture being configured for removable coupling with the cutting block; and
    a biased catch that is magnetized with a biasing force for securing the cutting block and capture together so that the cutting block and capture may be used with a cutting instrument for a surgical procedure,
    wherein the second guiding surface of the capture and the first guiding surface of the cutting block form a slot to guide a cutting instrument when the capture is coupled to the cutting block and secured by the magnetized catch,
    wherein the biasing force tends the catch toward a position for securing the cutting block and capture together when the catch is plied away from the position.

2. The apparatus of claim 1 wherein the biasing force comprises a magnetic force.

3. The apparatus of claim 2 wherein the cutting block is configured to couple with the capture in a plurality of distinct positions to form a cutting guide in each position.

4. The apparatus of claim 2 wherein the first guiding surface of the cutting block is configured for guiding a saw blade for a resection procedure.

5. The apparatus of claim 2 wherein the first guiding surface of the cutting block comprises an open face guide surface.

6. The apparatus of claim 5 wherein the first guiding surface comprises the open face guide surface when the capture is coupled to the cutting block and secured by the magnetized catch.

7. The apparatus of claim 2 wherein the cutting block comprises a plate and the capture further comprises mating surfaces configured to align with the plate such that when the plate resides between the mating surfaces movement by the capture relative to the block along a first axis is impeded.

8. The apparatus of claim 7 wherein the magnetized catch comprises a traversing pin and the cutting block comprises an aperture configured to receive the traversing pin such that when the traversing pin resides in the aperture, movement by the capture relative to the block at least along a second axis is impeded, the second axis being perpendicular to the first axis.

9. The apparatus of claim 8 wherein the cutting block further comprises a rib and the capture comprises a bisected tab with a slot mated for alignment with the rib such that when the rib resides in the slot movement by the capture relative to the block along a third axis is impeded, the third imaginary axis being perpendicular to the first and second axes.

10. The apparatus of claim 1 wherein the magnetized catch comprises a pin and a lever to adjust the pin.

11. The apparatus of claim 10 wherein the lever includes an integrated magnet.

12. The apparatus of claim 11 wherein the catch is integrated with the capture and the cutting block comprises an aperture to receive the pin.

13. The apparatus of claim 12 wherein the aperture is a recess in the first cutting edge.

14. The apparatus of claim 13 wherein the lever is formed of a non-magnetic material.

15. The apparatus of claim 1 further comprising a projection to maintain the catch in an unsecured position.

16. The apparatus of claim 15 wherein the projection is a cam for gradually changing the catch from a secured to an unsecured position.

17. The apparatus of claim 16 wherein the cam surface is formed of an outwardly facing surface of the capture.

18. The apparatus of claim 1 wherein the first guiding surface of the cutting block forms a part of a cutting slot of the cutting block.

19. The apparatus of claim 1 wherein the biased catch is configured so that the biasing force alternately holds the catch in a first unsecured position and a second secured position.

20. An apparatus for guiding a cutting tool during a surgical procedure comprising:
a cutting block having a surface for guiding a cutting tool, the cutting block configured to be fixable to bone to make a cut therein;
a detachable capture having another surface to guide the cutting tool, the detachable capture configured for coupling with the cutting block in a coupled position in which the surfaces combine to form a guide slot for the cutting tool;
a cam on said detachable capture having a projection to selectively secure and unsecure the cutting block and the detachable capture in the coupled position; and
a catch for engaging the cam for securing the detachable capture and the block in the coupled position,
wherein the catch includes a first portion for engaging the projection of the cam such that when the first portion and projection coincide, the catch secures the cutting block and the detachable capture in the coupled position, and
wherein the catch includes a second portion for engaging the projection of the cam such that when the second portion and projection engage, the detachable capture and the cutting block are not secured.

21. The apparatus of claim 20 wherein the catch comprises a magnetized component that provides a magnetizing force for actuating a coupling element to secure the cutting block and the detachable capture in the coupled position.

22. The apparatus of claim 21 wherein the cutting block comprises a plate and the detachable capture comprises opposing surfaces corresponding with the plate to limit movement of the detachable capture with respect to the cutting block along a first axis perpendicular to the opposing surfaces when the detachable capture and the cutting block are in the coupled position.

23. The apparatus of claim 22 wherein the cutting block comprises a rib and the detachable capture comprises a slotted tab corresponding to the rib to limit movement of the detachable capture with respect to the cutting block along a second axis perpendicular to the first axis when the detachable capture and the cutting block are in the coupled position.

24. The apparatus of claim 23 wherein the cutting block comprises an aperture corresponding to a pin of the catch such that when the pin resides in the aperture when the detachable capture and the cutting block are in the coupled position and the reciprocal portion of the catch and the projection of the cam coincide, the catch secures the detachable capture to the cutting block.

25. The apparatus of claim 24 wherein the catch further comprises a lever including an integrated magnet.

26. The apparatus of claim 25 wherein the lever is formed of a non-magnetic material.

27. The apparatus of claim 25 wherein the projection comprises a "v"groove.

28. The apparatus of claim 21 wherein the projection comprises a triangular shape.

29. The apparatus of claim 21 wherein the reciprocal portion of the catch comprises a triangular shape.

30. The apparatus of claim 20 wherein the catch and cam are configured such that a rotation of the catch by about 90 degrees transforms the detachable capture and the cutting block in the coupled position from being secured to unsecured.

31. A bone resection guide comprising:
a first cutting guide having a bone resection tool guiding surface;
a second cutting guide having a bone resection tool guiding surface, said first and second cutting guides capable of being releasably coupled with said resection tool guide surfaces facing one another; and
a catch mounted on one of said first and second cutting guides, said catch having a magnetically actuated coupling element selectively engageable with the other of said first and second cutting guides to prevent relative movement therebetween in at least one direction,
wherein the bone resection tool guiding surface of the first cutting guide and the bone resection tool guiding surface of the second cutting guide form a slot to guide a cutting instrument when the capture is coupled to the cutting block and secured by the magnetized actuated coupling element of the catch.

32. The guide of claim 31 further comprising a cam engageable with the catch, the cam having a projection for rotatably moving the catch along the cam to and from a position securing said first and second cutting guides with the magnetically actuated coupling element.

33. The guide of claim 32 wherein the magnetically actuated coupling element comprises a lever and magnet.

34. The apparatus of claim 33 wherein the catch and cam are configured such that a rotation of the catch by about 90 degrees retracts the catch to release said first and second cutting guides.

35. An apparatus for guiding a cutting instrument during a surgical procedure comprising:
- a cutting block with a first guiding surface against which a cutting instrument may engage during a surgical procedure;
- a capture having a second guiding surface against which a cutting instrument may engage during a surgical procedure, the capture being configured for removable coupling with the cutting block; and
- a biased catch with a biasing force for securing the cutting block and capture together so that the cutting block and capture may be used with a cutting instrument for a surgical procedure,
- wherein the biased catch is a magnetized catch and the biasing force comprises a magnetic force, and
- wherein the cutting block comprises a plate and the capture further comprises mating surfaces configured to align with the plate such that when the plate resides between the mating surfaces movement by the capture relative to the block along a first axis is impeded, and
- wherein the magnetized catch comprises a traversing pin and the cutting block comprises an aperture configured to receive the traversing pin such that when the traversing pin resides in the aperture, movement by the capture relative to the block at least along a second axis is impeded, the second axis being perpendicular to the first axis.

36. The apparatus of claim 35 wherein the cutting block further comprises a rib and the capture comprises a bisected tab with a slot mated for alignment with the rib such that when the rib resides in the slot movement by the capture relative to the block along a third axis is impeded, the third imaginary axis being perpendicular to the first and second axes.

37. An apparatus for guiding a cutting tool during a surgical procedure comprising:
- a cutting block having a surface for guiding a cutting tool, the cutting block configured to be fixable to bone to make a cut therein;
- a detachable capture having another surface to guide the cutting tool, the detachable capture configured for coupling with the cutting block in a coupled position in which the surfaces combine to form a guide slot for the cutting tool;
- a cam on said detachable capture having a projection to selectively secure and unsecure the cutting block and the detachable capture in the coupled position; and
- a catch for engaging the cam for securing the detachable capture and the block in the coupled position,
- wherein the catch includes a first portion for engaging the projection of the cam such that when the first portion and projection coincide, the catch secures the cutting block and the detachable capture in the coupled position, and
- wherein the catch includes a second portion for engaging the projection of the cam such that when the second portion and projection engage, the detachable capture and the cutting block are not secured, and
- wherein the catch comprises a magnetized component that provides a magnetizing force for actuating a coupling element to secure the cutting block and the detachable capture in the coupled position, and
- wherein the projection comprises a triangular shape.

38. An apparatus for guiding a cutting tool during a surgical procedure comprising:
- a cutting block having a surface for guiding a cutting tool, the cutting block configured to be fixable to bone to make a cut therein;
- a detachable capture having another surface to guide the cutting tool, the detachable capture configured for coupling with the cutting block in a coupled position in which the surfaces combine to form a guide slot for the cutting tool;
- a cam on said detachable capture having a projection to selectively secure and unsecure the cutting block and the detachable capture in the coupled position; and
- a catch for engaging the cam for securing the detachable capture and the block in the coupled position,
- wherein the catch includes a first portion for engaging the projection of the cam such that when the first portion and projection coincide, the catch secures the cutting block and the detachable capture in the coupled position, and
- wherein the catch includes a second portion for engaging the projection of the cam such that when the second portion and projection engage, the detachable capture and the cutting block are not secured, and
- wherein the catch comprises a magnetized component that provides a magnetizing force for actuating a coupling element to secure the cutting block and the detachable capture in the coupled position, and
- wherein the cutting block comprises a plate and the detachable capture comprises opposing surfaces corresponding with the plate to limit movement of the detachable capture with respect to the cutting block along a first axis perpendicular to the opposing surfaces when the detachable capture and the cutting block are in the coupled position, and
- wherein the cutting block comprises a rib and the detachable capture comprises a slotted tab corresponding to the rib to limit movement of the detachable capture with respect to the cutting block along a second axis perpendicular to the first axis when the detachable capture and the cutting block are in the coupled position, and
- wherein the cutting block comprises an aperture corresponding to a pin of the catch such that when the pin resides in the aperture when the detachable capture and the cutting block are in the coupled position and the reciprocal portion of the catch and the projection of the cam coincide, the catch secures the detachable capture to the cutting block, and
- wherein the catch further comprises a lever including an integrated magnet, and
- wherein the projection comprises a "v"groove.

39. An apparatus for guiding a cutting tool during a surgical procedure comprising:
- a cutting block having a surface for guiding a cutting tool, the cutting block configured to be fixable to bone to make a cut therein;
- a detachable capture having another surface to guide the cutting tool, the detachable capture configured for coupling with the cutting block in a coupled position in which the surfaces combine to form a guide slot for the cutting tool;
- a cam on said detachable capture having a projection to selectively secure and unsecure the cutting block and the detachable capture in the coupled position; and
- a catch for engaging the cam for securing the detachable capture and the block in the coupled position,
- wherein the catch includes a first portion for engaging the projection of the cam such that when the first portion and projection coincide, the catch secures the cutting block and the detachable capture in the coupled position, and wherein the catch includes a second portion for engaging the projection of the cam such that when the second portion and projection engage, the detachable capture and the cutting block are not secured, and wherein the catch comprises a magnetized component that provides a magnetizing force for actuating a coupling element to secure the cutting block and the detachable capture in the coupled position, and wherein the projection comprises a triangular shape, and wherein the reciprocal portion of the catch comprises a triangular shape.

* * * * *